United States Patent [19]

Dikstein

[11] 4,206,769
[45] Jun. 10, 1980

[54] MEASUREMENT OF SURFACE PROPERTIES

[76] Inventor: Shabtay Dikstein, 7 Habanai St., Jerusalem, Israel

[21] Appl. No.: 915,875

[22] Filed: Jun. 15, 1978

[30] Foreign Application Priority Data

Mar. 14, 1978 [IL] Israel .......................................... 54277

[51] Int. Cl.² ............................................... A61B 5/00
[52] U.S. Cl. .................................... 128/774; 73/432 R
[58] Field of Search ............... 128/774, 782, 643, 744; 73/432 R, 849, 64.4

[56] References Cited

U.S. PATENT DOCUMENTS 4,037,480 7/1977 Wagner ................................ 128/774

*Primary Examiner*—Willis Little
*Attorney, Agent, or Firm*—Browdy and Neimark

[57] ABSTRACT

The invention relates to a novel device for measuring in a quantitative manner surface properties, especially of tissues such as human skin, comprising a probe to be placed on said surface, means for applying a predetermined weight to said surface via said probe, means for removing the weight and means for measuring the change of height against time of the surface when the weight is removed. The probe may also be applied by suction and a force may be applied to it, tending to lift it from said surface, determining the change of height of the surface when said force is applied. The invention further relates to a method for determining surface properties, and especially elasticity, compressibility, viscosity, humidity and stretchability of human skin and for determining the effects of various cosmetic preparations on human skin.

17 Claims, 5 Drawing Figures

MEASUREMENT OF SURFACE PROPERTIES

FIELD OF THE INVENTION

The present invention relates to a novel device and to a method for testing qualitatively and quantitatively elasticity of tissues, and especially the elasticity of human skin. The device according to the invention comprises means for measuring elasticity and for recording graphically various parameters characteristic of the elastic properties of human skin.

BACKGROUND OF THE INVENTION

The elasticity of tissues varies and changes with age and is also influenced by various other parameters, such as health, fatigue, influence of exterior factors and the like. It is one of the main aims of therapeutic cosmetics to increase the elasticity and humidity of the skin, and thus to restore its youthful appearance and to prevent formation of wrinkles. According to the present invention an objective method of measurement is provided, which makes possible to evaluation of the elasticity of human skin in vivo before and after application of certain cosmetic preparations, thus providing both an objective test for the efficacy of such preparations and for their effect on the individual treated with same.

According to the present invention a sensitive instrument is presented which makes possible accurate measurements, providing data which are valuable in accurate evaluations of measurements of compressibility, humidity, viscosity and elasticity, and thus of the effects of various cosmetic preparations.

The novel instrument comprises mechanical and/or magneto-electronic means for the measurement of certain parameters indicative of the elasticity of tissues, and especially of human skin, in vivo, and especially in the lower part of the stress-strain curve of such tissues.

According to a further feature of the present invention means are provided for evaluation of the stretchability of human skin by applying a small predetermined pull on the skin in vivo. According to a preferred embodiment the contact of the probe with the skin is maintained by the application of vacuum-suction. The results thus obtained are indicative of the condition of the skin and also related to the quantity and nature of wrinkles.

The probe is applied to the tissue which is being tested, and vacuum is applied via a conduit in the probe and certain values thus measured are also indicative of parameters connected with the elasticity of the tissue. Further features of this novel and specific embodiment will be illustrated hereinafter.

The device according to the present invention is a modification of the instrument described by H. Schade, Z. fuer exp.Pathol. u. Therapie, 11, (1912) 369-399 and permits accurate measurement in a range of values substantially lower than the standard one used by Schade for his measurements, namely about 100 g/cm$^2$. Furthermore, according to a preferred embodiment of the present invention means are provided for also carrying out measurements involving the application of suction (by applying a vacuum via the probe).

The probe of the novel instrument comprises a measuring area of the order of about 3 to 8 mm diameter, and preferably of about 5 mm diameter, which is about 0.2 cm$^2$ area. The surface of the probe is advantageously an inert plastic material, such as Teflon or the like, and according to the preferred embodiment providing for the application of suction, it is provided with a throughgoing conduit, and in this case the surface of the probe advantageously slopes inwardly, thus forming a funnel-shaped structure which facilitates the application of suction.

The probe is connected to a light measuring rod, which may be made of light metal, and which is counterbalanced so as to apply only a light load, the pressure of the system not exceding about 1 g/cm$^2$. Means are provided for applying weights to the measuring rod, thus providing for the possibility to increase the starting pressure to a predetermined value. The measuring rod is connected to a suitable measuring device of high sensitivity and low inertia, thus making possible measurements in the lower range of the stress-strain curve. Advantageously the measuring rod is connected to a Linear Variable Differential Transformer (LVDT), means being provided for recording the output of the LVDT with adequate sensitivity. Recording means were tested giving about half-scale deflection per 1 mm indentation for a certain range of measurements. A recorder having a moving sheet of recording medium was used. The speed of movement of the paper can be adjusted according to the accuracy of the record desired.

The invention is illustrated by way of example only with reference to the enclosed drawings in which.

Figure 1:
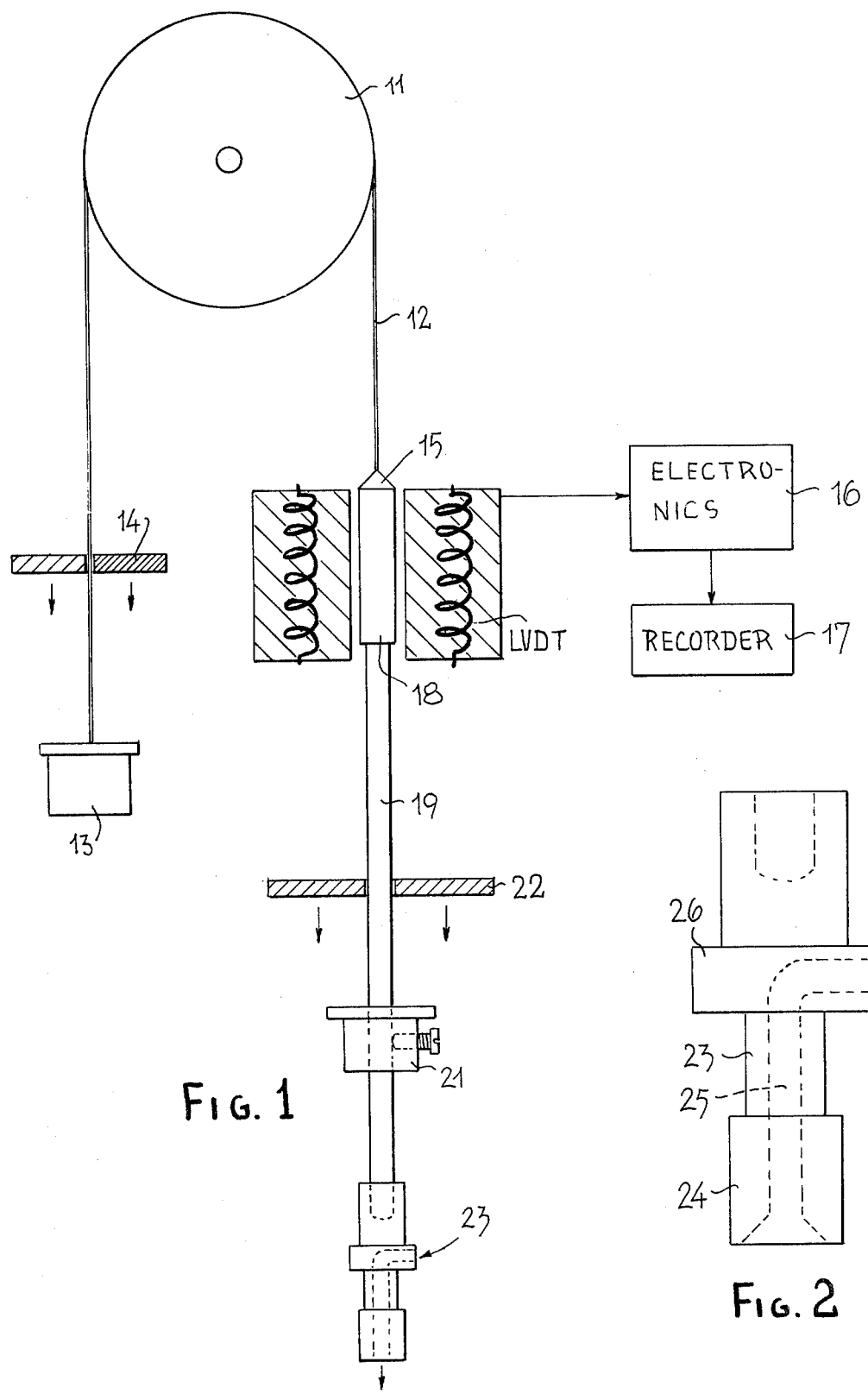
FIG. 1 is a schematical side view, in partial section, not according to scale, of a device according to the invention.
Figure 2:
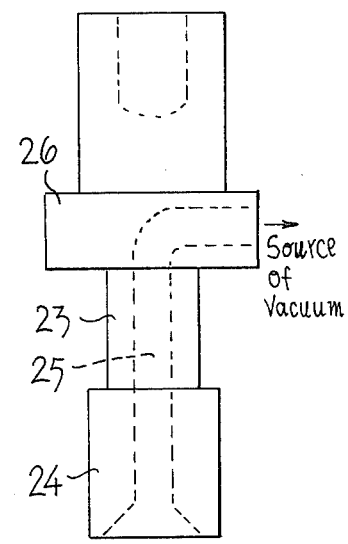
FIG. 2 is a schematical enlarged side view of the probe and its carrier, which is used in the device of FIG. 1.

As shown in the enclose Figures, the device comprises in combination a pulley 11 over which there passes the wire 12, connected on the one side to member 13, adapted to support the removable weight 14, and connected at its other end to the LVDT indicator 15, which is connected with electronical conversion means 16 attached to the recorder 17, the central movable member 18 of the LVDT device being attached to the rod 19, to which there is attached the removable member 21 adapted to support the weight 22, and which terminates in the probe 23, which is shown in detail in FIG. 2. This probe comprises a lower funnel-shaped member 24 made of Teflon, and which defines a lower circular member of about 5 mm diameter. There is provided a throughgoing hole 25 which can be connected to a vacuum source via connection 26.

Two different measurements can be effected with this novel device:

a. Indentation measurements, where the probe is placed on the surface to be tested, the counterweight is balanced so as to establish a pressure of about 1 g/cm$^2$ on the surface, the recorder is actuated, and after a certain short period of time the weight 22 is applied to member 21, the weight is left in place for a certain time, it is removed and the change of height of the probe is further recorded for some additional seconds. The record of the entire procedure—rest, application of weight, removal and additional period, provides valuble information on the nature of the surface to which the probe is applied.

For effective measurements of the stratum corneum the pressure is chosen to be in the range of about 2 g/0.2 cm² of the probe.

The second type of measurement is effected by applying the probe to the surface, applying vacuum to cause adhesion of the probe to the skin, applying a weight to the support 13, recording the change of height, maintaining it for a certain period and removing the weight, while recording the change of height of the probe.

Human skin was tested in vivo with various volunteers, and the test was carried out while the volunteer lies on his back. The probe 23 is positioned in a manner so as to touch the skin on the middle of the forehead, with the surface of the probe in touch with the skin. The baseline of the measuring device is stabilized for about 15 seconds, and after this period of time a predetermined weight is applied rapidly. The weight applied was varied within a certain range, good results being obtained with a weight of about 2 g for the probe of 0.2 cm² surface area. The indentation of the tissue resulting from the application of this force is recorded for a certain period of time, of about 5 to 30 seconds, preferably about 15 seconds and at the end of the predetermined period the load is suddenly removed and the rebounce of the tissue is recorded for a certain period, also of the order of 5 to 30 seconds and preferably about 5 to 15 seconds.

Measurements were effected as follows:

a. The probe was applied and balanced at a net load of 1 g/cm² (the area of the probe was 0.2 cm²); the electronic system is zeroed and the recorder is started at a speed of 6 cm/min;

b. the baseline is stabilized for 15 seconds;

c. a weight of 2 g (i.e. 10 g/cm²) is applied (in position A) suddenly and the recording of the resulting indentation is carried out for 15 seconds;

d. the weight is removed and the rebounce is recorded for 15 seconds.

From the above graphs, the following parameters were evaluated: R which is the percent rebounce of the tissue 6 seconds from the removal of the weight indicating the relative importance of the elastic elements; I max which is the maximum indentation resulting from the application of the weight and which is inversely related to skin humidity.

Various cosmetic preparations, lotions and other substances were tested. Certain raw materials employed in cosmetical preparations were applied in the form of 10% either in water or in alcohol, according to the solubility of the substance. The solution was applied by means of cotton wool to the skin of the forehead and the indentation curve was recorded in intervals of half an hour after the treatment. The effect of water and alcohol disappears after 30 minutes; skin was chosen so that no wrinkle passed through the measured area. Generally values obtained varied by no more than about 10% during repeated measurements with the same substances.

Normal skin values were measured with volunteers and the values obtained with a standard pressure of 10 g/cm² were $I_{max}=0.3$ to 0.8 mm; R: 40 to 90%. Measurements with various pressures indicate that within the range of 10 to 40 g/cm² pressure the resulting indentation is linearly related to the square root of the applied pressure.

Satisfactory results could not be obtained when a pressure as high as 40 g/cm² was used. From the work of Schade it is clear that he had to use comparatively high pressures, well in excess of this value due to the lack of sensitivity of his measuring device and due to its mechanical inertia. At pressures used by him rather large indentations are obtained and these are not indicative of the properties of the outer layer of the skin, namely the stratum corneum which is the layer responsible for the properties of the skin which are of importance to be measured according to the present invention. It is clear that Schade measures values resulting from the mixture of properties of more than the uppermost skin layer, and gives only an average value of the various layers, which is not indicative of the properties we are interested in. According to the present invention, due to the substantially increased sensitivity and thus lower pressure required for accurate measurements, it has become possible to measure the properties of the uppermost skin layer.

Figure 3:
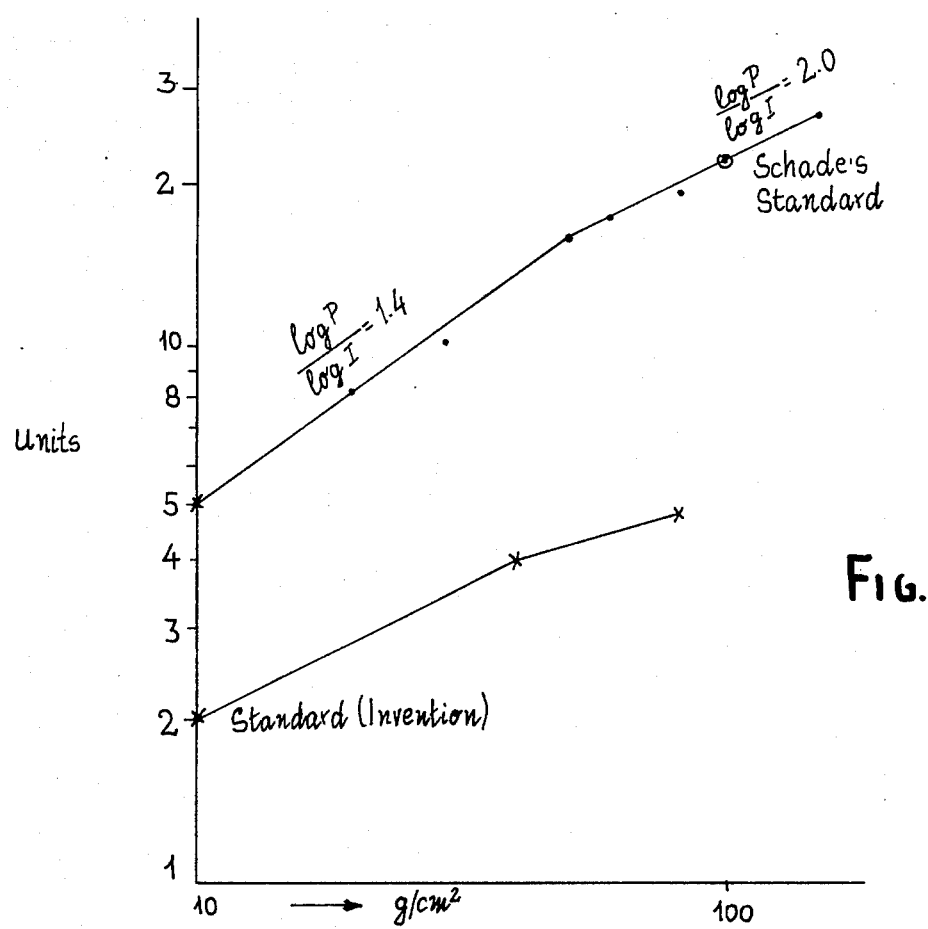
FIG. 3 is a graphical representation of indentometric curves, of indentation against pressure.
Figure 4:
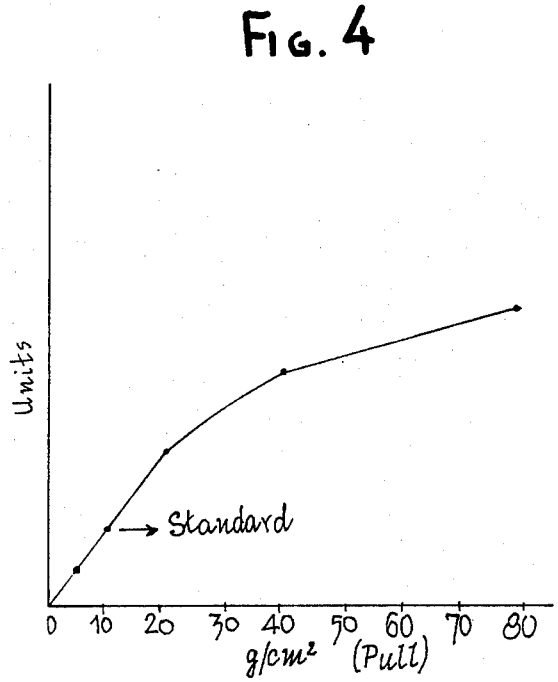
FIG. 4 is a graphical representation of a levarometric measurements of elevation against pull.
Figure 5:
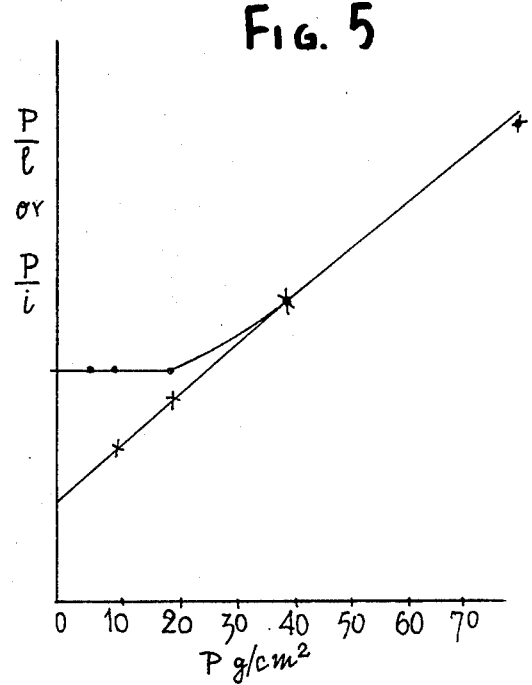
FIG. 5 is a graphical representation of pressure divided by indentation or elevation against pressure or pull.

From the enclosed plots (see Indentometry FIGS. 3, 4 and 5) of an individual skin (according to the method of Oesterle - Jocca 58, 21 (1975) it is quite clear, that indentation and pull are only different elasticitywise if one uses less than 20 gm/cm² pressure or pull.

According to another embodiment of the present invention measurements are carried out in order to evaluate the stretchability of the skin. A standard pull is applied to the skin, and the values obtained are indicative of the capability of the skin to undergo stretching. The same probe is used, and this is provided with means for applying a vacuum, thus attaching the probe to the skin. The probe is applied to the skin, if possible to a surface thereof free of wrinkles and the probe is balanced in such a manner that a weight of about 1 g/cm² is applied. The vacuum is applied, and thus the probe is secured to the skin; the instrument is zeroed and a weight is applied to the other arm of the instrument, thus applying a predetermined pull on the skin. A weight of 2 g was chosen for the probe area of 0.2 cm². This state is maintained for about 10 to 15 seconds, so as to establish an equilibrium, while the recorder is actuated. At the end of this period the weight is removed, and this results in the substantially immediate return of the skin to the starting position. The elevation of the skin due to the application of the weight indicates the stretchability of the skin. Values within a certain range are about linear. This is true for the range of up to about 20 g/cm²; see enclosed FIGS. 2 and 3. The result of various cosmetics on the elevation thus obtained was tested. It is assumed that less than 20% effect after 60 minutes can be considered as lack of significant effect of the tested substance.

Amongst the important advantages of the present invention there may be mentioned that the device and method according to the invention provide the possibility for an objective measurement and evaluation of properties of human skin which are of use in testing and evaluating cosmetics;

it makes possible to evaluate the properties of the skin of individuals in vivo and especially parameters related to elasticity, compressibility, humidity and stretchability;

It provides the possibility to evaluate the effectivity of cosmetics in general and on individuals in vivo in particular;

it makes possible to evaluate the efficiency of novel cosmetic preparations and thus to develop improved preparations;

it makes possible to establish certain cathegories of skin types and their response to certain cosmetics.

It ought to be mentioned that the invention is described with reference to testing of properties of human skin, but that the device and method are not restricted to such measurements as it is possible to use the novel instrument for the testing and quantitative evaluation of various other subject matter, such as for example in agricultural applications where it can be used to determine the ripeness of certain fruit and vegetables and the like.

I claim:

1. A device for accurate measurements of properties of a passive surface, such as human skin, the device comprising:
   (a) a probe one end of which is to be placed on a passive surface whose properties are to be measured;
   (b) means coupled to a second end of said probe for selectively applying a predetermined pressure via said one end of said probe to the surface of the order of from 5 g/cm$^2$ to 40 g/cm$^2$ and for reducing said pressure to at least to a given lower pressure;
   (c) sensing means coupled to said probe and responsive to its position for providing an output signal representative of height change of said surface against time when said predetermine pressure is applied and reduced; and
   (d) means coupled to said sensing means for recording the output signal therefrom.

2. A device according to claim 1, wherein said sensing means is a linear variable differential transformer (LVDT).

3. A device according to claim 1, wherein that end of the probe which is to be placed against the surface whose properties are to be measured has a surface area of 0.1 to 1.0 cm$^2$ area.

4. A device according to claim 1, wherein a conduit is provided in the probe, ending in the surface thereof which is to be positioned on the surface to be measured, and including means for attaching said probe to a source of vacuum, thereby providing the possibility of attaching the probe by suction to the surface whose properties are to be measured.

5. A device according to claim 4, including means for applying a predetermined force to said probe resulting in a force on said probe which lifts said probe from the surface to which it is attached by vacuum, and wherein said sensing means produces an output signal indicative of the resulting difference of level of the probe.

6. A device according to claim 1, wherein said means for applying a predetermined pressure comprise means for applying a force in either direction providing a pressure of the order of 2 g per 0.2 cm$^2$ surface area of that end of the probe which is to be placed against the surface whose properties are to be determined.

7. A device according to claim 4, wherein the probe is provided at its end with a funnel-shaped opening, connected to the vacuum source via said conduit.

8. A device according to claim 1, wherein said sensing means comprise electro-magnetic means, including a movable core rigidly connected to said probe.

9. A device according to claim 8, wherein said means for selectively applying a predetermined pressure include at least one member having a weight-receiving surface and being mechanically coupled to said core, and at least one removable weight positionable or said weight-receiving surface.

10. A device according to claim 1, including a second member having a second weight-receiving surface mechanically coupled to said core, and at least one additional removable weight which positionable on said second weight-receiving surface, said second member being coupled to one end of said core and said at least one member being coupled to the other end thereof.

11. A method for accurate measurement of properties of a passive surface such as elasticity, the method comprising applying a probe so as to establish a pressure of predetermined value to said passive surface, adapted to result in changes in substantially only the surface layer to be measured, recording the change of level of the probe resulting from the application of said pressure to said passive surface, removing at least a portion of the predetermined pressure and recording the resulting change of said level.

12. A method for accurate measurement of surface properties such as elasticity which comprises applying a probe so as to establish a pressure of predetermined value to said surface, adapted to result in changes in substantially only the surface layer to be measured, recording the change of level of the probe resulting from the application of said pressure, removing the pressure and recording the resulting change of said level, and wherein the surface is the epidermis, and the pressure is applied of less than 20 g/cm$^2$ probe area by a weight.

13. A method according to claim 12, wherein the probe is of about 0.2 cm$^2$ area of the weight applied is between 1.0 g and 2.0 g.

14. A method for the accurate measurement of surface properties such as elasticity which comprises applying a probe so as to establish a pressure of predetermined value to said surface, adapted to result in changes in substantially only the surface layer to be measured, recording the change of level of the probe resulting from the application of said pressure, removing the pressure and recording the resulting change of said level, and wherein the probe is applied by suction to the surface, properties of which are to be measured, a weight is applied in a direction tending to lift the probe from the surface, and the resulting change of level of the probe is recorded versus time.

15. A method according to claim 14, wherein the measurement is carried out on human skin, said measurement being for evaluating the effects of cosmetic preparations on human skin, which comprises applying such preparation to human skin in vivo, and recording the surface properties of the skin at predetermined periods of time, comparing said properties before such application and at certain periods of time after such application.

16. A method for the accurate measurement of surface properties of human skin which comprises applying a probe so as to establish a pressure of predetermined value to said surface, adapted to result in changes in substantially only the surface layer to be measured, recording the change of level of the probe resulting from the application of said pressure, removing the pressure and recording the resulting change of said level, measured are compressibility, viscosity, elasticity, humidity and stretchability of the human skin.

17. A method for the accurate measurement of surface properties such as elasticity which comprises applying a probe so as to establish a pressure of predetermined value to said surface, adapted to result in changes in substantially only the surface layer to be measured, recording the change of level of the probe resulting from the application of said pressure, removing the pressure and recording the resulting change of said level, and wherein the measurement is carried out on human skin, said measurement being for evaluating the effects of cosmetic preparations on human skin, and which comprises additionally applying such preparation to human skin in vivo, and recording the surface properties of the skin at predetermined periods of time, comparing said properties before such application and at certain periods of time after such application.

* * * * *